United States Patent [19]

Levene et al.

[11] Patent Number: 4,821,727

[45] Date of Patent: Apr. 18, 1989

[54] MAMMOGRAPHIC BIOPSY NEEDLE HOLDER SYSTEM

[75] Inventors: Simha Levene, Tiberias; Dan Inbar, Haifa, both of Israel

[73] Assignee: Elscint Ltd., Haifa, Israel

[21] Appl. No.: 924,628

[22] Filed: Oct. 30, 1986

[51] Int. Cl.⁴ .............................................. A61B 6/00
[52] U.S. Cl. ..................................... 128/653; 378/16; 378/37; 378/108; 378/208
[58] Field of Search ........................ 128/653, 654, 659; 378/37, 68, 16, 17, 97, 108, 177, 180, 208

[56] References Cited

U.S. PATENT DOCUMENTS

| | | | |
|---|---|---|---|
| 3,803,417 | 4/1974 | Kok | 378/196 |
| 3,971,950 | 7/1976 | Evans et al. | 378/180 |
| 4,020,347 | 4/1977 | Geluk | 378/37 |
| 4,051,377 | 9/1977 | Kemner et al. | 378/16 |
| 4,087,694 | 5/1978 | Hellstrom et al. | 378/195 |
| 4,246,607 | 1/1981 | Vijuerberg | 128/653 |
| 4,260,894 | 4/1981 | Neumann | 378/16 |
| 4,366,575 | 12/1982 | Bax | 378/16 |
| 4,544,949 | 10/1985 | Kurihara | 128/654 |
| 4,599,738 | 7/1986 | Panetta et al. | 378/37 |
| 4,649,558 | 3/1987 | Brunn et al. | 378/108 |

FOREIGN PATENT DOCUMENTS 2640248  3/1978  Fed. Rep. of Germany ........ 378/37

OTHER PUBLICATIONS

Article: Mammographic Needle Localization of Lesions Seen in Only One View by Rauf Yagan et al., pp. 911-916, Mday 1985, American Journal of Radiology, vol. 144, (American Roentgen Ray Society).

Primary Examiner—Ruth S. Smith
Attorney, Agent, or Firm—Sandler & Greenblum

[57] ABSTRACT

An X-ray mammographic biopsy needle holder positioning system wherein the X-ray source is tilted to provide parallax views of the needle holder inserted in the breast. The tilting occurs independently of the breast compressor which remains untilted.

6 Claims, 5 Drawing Sheets

MAMMOGRAPHIC BIOPSY NEEDLE HOLDER SYSTEM

FIELD OF THE INVENTION

This invention is concerned with radiogaphic imaging systems and more particularly with such systems used to assist in locating growths for the surgeon in mammallary biopsy procedures.

BACKGROUND OF THE INVENTION

X-rays have long been used to acquire images of the internal functioning of the patient's body for diagnostic purposes. More recently X-ray equipment has been used for assisting in invasive techniques such as biopsies and lithotripsy. For example, in X-ray mammography the breast of the patient is X-rayed and X-ray films are closely viewed to determine whether there are any microcalcification or other growths (hereinafter generally termed "lesions".) If a lesion is discovered then it is necessary to determine if it is a benign growth or if it requires immediate treatment. For such a determination is it often necessary to perform a biopsy to finally determine whether the lesion discovered in the X-ray image is pathological or benign. The radiologist performs a needle localization procedure whereby he inserts a radio opaque needle into the center of the susceptor growth to indicate to the surgeon the tissue to be excised. More particularly, the patient is brought to the mammographic system. The breast is compressed between horizontal plates attached to the X-ray equipment C-arm. The C-arm is a "C" shaped bracket which normally holds the X-ray tube at the top and the X-ray beam receptor at the bottom. The raiologist marks the breast or one of the compression plates at a point in a plane where he thinks the lesion is located, based on the study of the preliminary X-ray. An X-ray image is taken and developed to determine whether the marking is indeed in the correct location. If it is not in the correct location, then the radiologist repeats the marking procedure, acquiring another X-ray image. When the marking is indeed aligned with a lesion, the radiologist inserts the holder of the lesion-locating needle into the compressed breast through an aperture or recess in the compression plate at the marked point so as to center the holder tip within the lesion that was observed in the preliminary X-ray.

The breast is then removed from the compression plates and the C-arm is rotated 90 degrees, the breast is again compressed but now the compression plates are vertically aligned. Another X-ray is acquired to check the alignment of the needle holder tip and the lesion in the horizontal plane to assure that the holder tip is indeed within the lesion. If the holder tip is not within the lesion, or sufficiently close, the needle holder is moved and another image is acquired. The process is repeated until coincidence is obtained. Then the needle is inserted into the holder and the holder is withdrawn.

Thus in the prior art X-ray mammography a plurality of X-ray images and a plurality of breast clamping operations are required to position the needle holder to locate the lesion for the surgeon. The repeated operations are time consuming and uncomfortable for the patient and subject the patient to the X-ray dosage required to acquire the many images over a substantial area of the breast.

Radiologists and scientists have been seeking to improve the biopsy needle-positioning procedure. For example, the positioning procedure outlined hereinabove applies when the lesion can be seen in two orthogonal views. Sometimes the lesion can only be seen in one view. In March of 1984 a presentation at the National Conference on Breast Cancer of the American College of Radiation described a technique for a mammographic needle localization of lesions which cannot be imaged in two orthogonal views, but only in one of them. In this technique the X-ray beam is moved 30 degrees in a xeromammographic system where there is no breast clamping. An article describing the presentation appeared in the American Journal of Radiology Vol 144, pp 911–916, May 1985. The article describes a method that does not use C-arm clamping, and where by it is possible to locate the needle using images taken at two positions at 30 degrees apart.

Mammographic compression devices for normal X-ray film mammographic systems originally started with what may be described as dependent compression. At the top of the C-arm there was an X-ray tube and collimator arrangement which served as the source of the beam. A cone extended from the soruce to the breast to compress the breast against the X-ray radiation receptor or film at the bottom of C-arm. Thus the compression means i.e. the cone was fixedly attached to the C-arm. The movable film container provided the other side of the compression means. Rotating the C-arm also rotated the compression means.

Subsequently, movable compression plates were attached to the C-arm between the X-ray source at the top of the C-arm and the X-ray receptor (i.e. the film) at the other end. The movable compression plates were movably attached along the longitudinal axis of the C-arm to adjust to the woman's breast. In this arrangement the compression plates rotate with the C-arm. Thus, this arrangement also requires unclamping and reclamping the breast when the C-arm is rotated, even through small angles.

Compression plates are important in mammography to improve the quality of the image and to thereby enable the discovery of more lesions. When the breast is compressed it flattens and absorbs the X-ray beam less, and more uniformly. In addition extraneous movements are eliminated. These beneficial results of clamping improve the quality of the image. Therefore, it is highly desirable to compress the breast for mammographic breast image processing.

From the above description of the prior art it is readily understood that it would save time and reduce patient discomfort if a system could be provided that generates an immediate image to aid in positioning the lesion-locating needle holder for biopsy purposes. It would save further time and discomfort if it could utilize a single clamping position, and avoid movements of the lesion during reclamping with consequent relative movement of needle holder and lesion.

Until now, imaging chains have not been used for invasive mammographic techniques such as for positioning the biopsy locating needle. Until now the prior art systems using breast compression means have rotated the X-ray beam through 90 degrees for ascertaining that the needle holder tip is indeed within the lesion. The prior art systems have used an X-ray film means for acquiring images. When films are used as the X-ray receptor, waiting periods for the developing of the films are required before the radiologist can proceed with the next step in properly positioning the needle.

Accordingly, it is an object of the invention to provide mammographic biopsy needle positioning system using a radiographic imaging chain for providing the image which indicates the location of the needle holder.

It is also an object of the invention to provide in a system for positioning a biopsy needle locator in an X-ray mammographic system means for tilting the X-ray beam to obtain a parallax view of the needle holder and the breast without having to move the breast compression means when moving the beam. The system is designed to locate the biopsy needle in a minimum of time with a minimum of X-ray dosage and a maximum of accuracy.

BRIEF DESCRIPTION OF THE INVENTION

In accordance with the present invention a mammographic biopsy needle holder positioning system is provided, said system comprising:

X-ray tube means for generating X-ray beams directed to pass through the breast of a patient, collimating means for limiting the X-rays passing through the breast to small areas, breast compression means for compressing the breast in a direction to decrease and make uniform the path length in the breast through which the X-ray beams pass, X-ray receptor means on the side of the breast opposite the X-ray source, means for tilting said X-ray source a sufficient amount to obtain a parallex view of the biopsy needle holder inserted into the breast, and said compression means being uncoupled from said means for tilting said X-ray source.

A feature of said compression means is that they are adjustably mounted relative to the X-ray beam to enable centering the suspected lesion on the x-ray beam axis without the need to release the breast compression.

Also in accordance to the present invention a mammographic biopsy needle holder locating system is provided, said system comprising:

X-ray source means for generating X-rays directed to pass through the breast of a patient, collimator means for limiting the X-rays passing through the breast to small areas, means for compressng the breast substantially in the direction of the X-ray beams, means for tilting the X-ray source for obtaining images of the breast from more than one angle, X-ray receptor means located on the side of the breast opposite the X-ray source, and said X-ray receptor means comprising an X-ray imaging chain.

A feature of the invention comprises the use of high resolution means in said imaging chain. Thus said imaging chain comprises a high resolution, small diameter, fluorescent screen and means for optically placing said fluorescent screen in the path of the X-rays which have passed through the breast; a high resolution image intensifier; a high resolution TV camera for providing video signals responsive to the output of the image intensifier which operates responsive to the signals from the fluoroscent screen.

The imaging chain enables instantaneous views of the needle or the needle holder as it is inserted into the breast. This eliminates the necessity of the X-ray film, among other things, and the time required for its chemical development.

A feature of the invention includes optically coupling said image intensifier to said fluoroscent screen over a folded optical path.

A related feature of the present invention comprises reflecting means (for coupling between the fluorescent screen and the image intensifier) mounted juxtaposed to the junction area between the breast and the chest wall; thereby enabling imaging of an area not otherwise obtainable using imaging chain equipment.

Another feature of the invention comprises optically coupling said images intensifier to said video camera through a beam splitter.

Yet another feature of the invention comprises an analog-to-digital conversion means coupled to a frame grabber or frame store means and enabling presentation of the image acquired during X-ray exposure after the exposure has been completed.

Yet another feature of the invention reduces the radiation dosage by using an unique incremental dosage system which averages the accumulated signal strength per repeated exposure until a desired image quality is acquired.

Still another feature of the invention comprises the use of stereo imaging means for acquiring a stereo image of the breast during the biopsy needle holder positioning process to thereby enhance the ability of the doctor to obtain a biopsy specimen from the desired section of the breast and to reduce the time required for the process.

BRIEF DESCRIPTION OF THE DRAWINGS

The above mentioned and other features and objects of the present invention will be best understood when considered in the light of the following description made in conjunction with the accompanying drawings, wherein.

GENERAL DESCRIPTION

Figure 1:
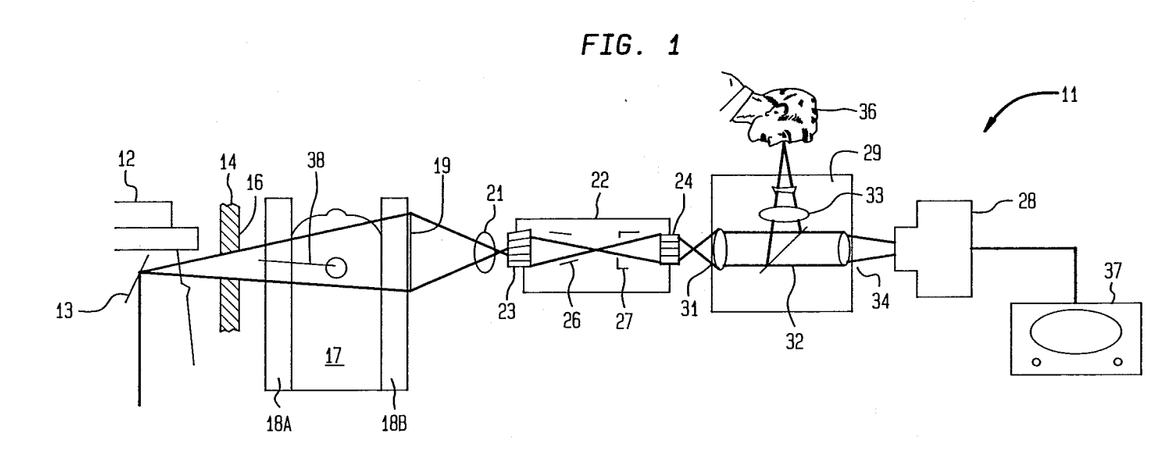
FIG. 1 is a block diagram of a mammographic fluoro-biopsy needle holder positioning system.

The mammographic imaging chain system 11 of FIG. 1 includes an X-ray tube means 12. Preferably it is a micro-focused type X-ray tube. The tube includes an X-ray target 13, to which the X-rays are directed for transmission through an X-ray collimator 14. The collimator has an aperture 16 therein; relatively a small size can be used since the beam merely has to encompass the lesion and a small area there about. The small size improves image quality by minimizing scatter, for example; it also reduces the dose.

The patient's breast is shown as 17 located between two compression plates 18a and 18b. On the side opposite to the collimator side of the breast is a fluorescent screen 19. The fluorescent screen detects X-ray radiation passing through the breast and responsive to the detected X-ray photons releases light photons.

Means are provided for coupling the fluorescent screen to an image intensifier. More particularly the light photons are focused by lens 21 onto an optical image intensifier 22. The optical image intensifier is commercially available and has a luminance gain of 100 to 100,000. The specific model shown is an AEG XX 1066 and in the preferred embodiment has a fibre optic input 23. Electron lenses direct the image onto an electrode 24 associated with a fluorescent screen.

Between the fibre optic input 23 and the output electrode 24 are a pair of lens electrodes 26 and 27 used to direct and focus the image onto the output screen. The output of the intensifier 24 may be optically coupled to a video camera 28 through an image distributor 29. It should be understood that other means may be provided such as direct coupling of video camera and the image intensifier. This distributor includes a collimator lens 31 and a 90% partial reflector 32. The reflector splits the image between an eyepiece 33 and a TV camera lens 34. The eyepiece image is viewable by the clinician or doctor depicted as 36. The output of the video camera 28 is directed to a monitor 37. Thus the image may be viewed directly through the image distributor or displayed on the monitor.

A biopsy needle holder 38 is shown inserted into the breast and aligned with a lesion in a plane normal to the pressure plates. However, it could be aligned with, in front of or behind the lesion in the plane of the lesion parallel to the compression plates. FIG. 1 shows a fluoroscopically assisted biopsy needle holder positioning system comprising a small field of view as determined by the aperture of the collimator. The small field of view enables using a low dose and suffering very low scatter. Note that in FIG. 1 the fluorescent screen may be juxtaposed to the image intensifier input fiber optics, if it is in optical contact therewith.

When the lesion being examined is at the junction of the beast and the chest wall, there is no room for the fluorescent screen to be placed to obtain an image of the lesion. The situation is remedied in the embodiment shown in FIG. 2. More particularly FIG. 2 at 41 shows a fluoroscopically-assisted mammographic biopsy system; including an X-ray tube 42 mounted on one side of the collimator 43. The collimator has an aperture 44 therein which limits the field of view or the area upon which the X-rays impinge. The breast of the patient 46 is shown located between a pair of compression plates 47a and 47b.

Figure 2:
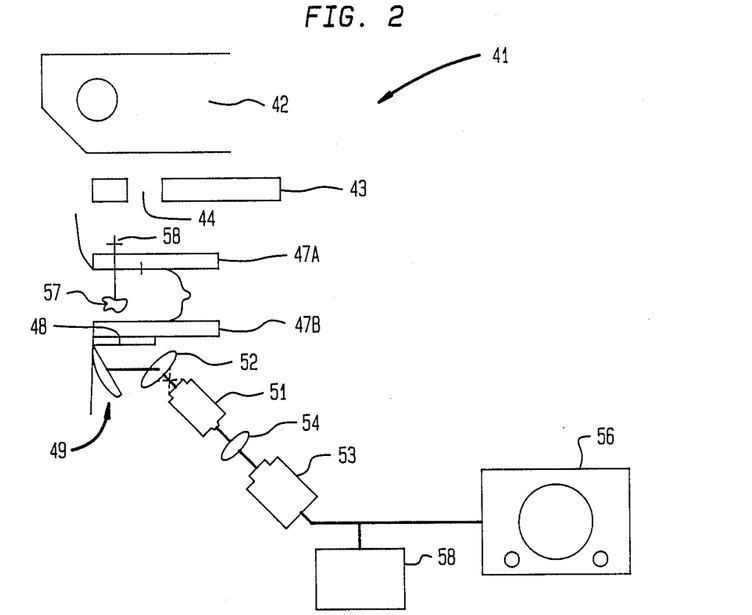
FIG. 2 is a block diagram of another embodiment of the system of FIG. 1.

Means are provided for collecting photons even in the area of the breast close to the chest wall. More particularly, a fluorescent screen 48 is shown mounted juxtposed to the breast and normal to the chest wall. Some of the light photons emitted from the fluorescent screen fall upon a mirror or prism 49 optically coupled to the image intensifier 51 through an optical lens system shown at 52. The image intensifier preferably is a one-inch type, high-resolution intensifier e.g. 320 line pairs per centimeter. Of course, a similar system in which the lens 52 is placed between the fluorescent screen 48 and the mirror 49 may sometimes be advantageously used. While the mirror or prism 49 is shown, the fluorescent screen output could be coupled to the image intensifier through fiber optic means.

The output of the image intensifier is optically coupled to a high resolution video camera 53 through a lens system 54. The lens system may include an image splitter such as that shown in FIG. 1; however, the image splitter is not necessary to the invention. The video camera 53 is coupled to a display monitor 56. Image processing means may be provided which process the data to provide the image. The processing means preferably include a frame grabber frame holder or frame memory means.

The biopsy needle holder arrangement is shown in FIG. 2 in schematic fashion at 57. The needle holder as shown may be moved to be inserted anywhere in the horizontal plane. Thus, it can be positioned so as to be inserted into lesion wherever it is. The folding mirror 49 enables obtaining the light photons from the fluorescent screen even when the lesion is near the chest wall. The difficulty of obtaining proper images near the chest wall is especially great when the images are fluoroscopically obtained and where the output of the screen has to be directed to an intensifier. Even when a small intensifier is used the diameter of the intensifier itself limits images that can be obtained from lesions that are close to the chest wall.

Figure 3A:
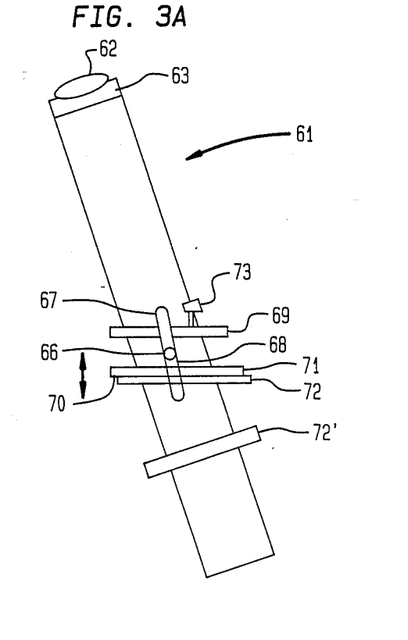
FIG. 3a shows decoupled, independent breast compression plates for use with small angle biopsy needle holder positioning systems.

FIG. 3a shows a decoupled independent compression means, more particularly the C-arm, assembly 61. At one end of the C-arm the source of the X-ray beam is shown as X-ray tube 62 and collimator means 63. The collimator means is used in this invention to limit the area of the breast upon which the X-ray beam impinges. It is possible to limit the area in this system since the radiologist is only interested in imaging an area around lesions that are to be recepient of the needle. The C-arm 61 tilts about a pivoting axis shown at 66, i.e. it pivots around an axis that is normal to the plane of the paper on which the drawing is made. Compression means 69 and 71 do not tilt with the C-arm but are (as schematically shown in FIG. 3A) attached to the vertical standards 67 and 68. These are fixedly attached to the nonrotating part of the mammographic unit.

The compression plates can be moved in the horizontal plane to align the area of interest (the lesion) with the axis of the X-ray beam. The movement means are indicated at 76 and 79 and described in greater detail with FIG. 4.

Figure 4:
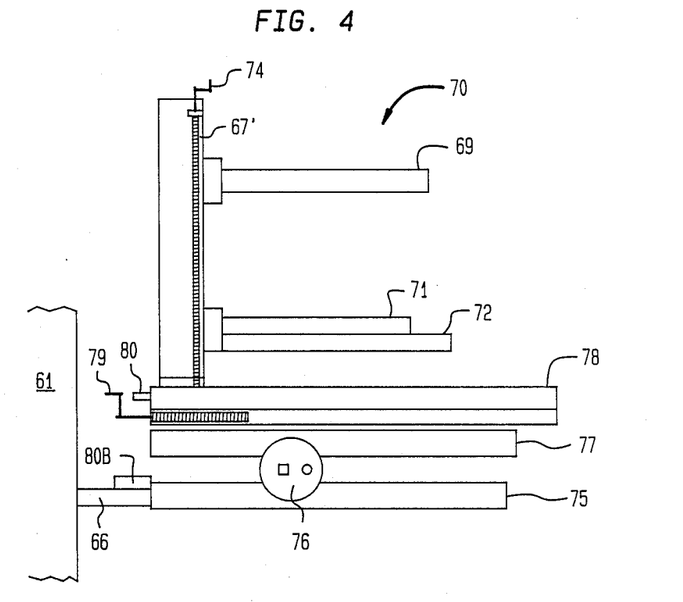
FIG. 4 shows an arrangement for adjustably moving the breast compression means in the horizontal plane.

In FIG. 4 the compression plates 69 and 71 are shown as attached to the standard 67'. These compression plates are movably attached to the standard so as to be able to compress the breast. On the side of the breast opposite the source of the X-ray beam there is provided an image receptor means shown at 72. the image receptor means may be an X-ray film-screen or xerographic cassette or a fluorescent screen which may be part of an imaging chain.

The image receptor of the X-ray is shown in a nonmagnifying position, i.e. juxtaposed to the lower compression plate 71 in FIG. 3a. At 72' in this figure there is shown an image receptor means which is removed from the lower compression plate and therefore provides magnification. The magnification is the ratio of the distance of the X-ray beam source from the compressed breast as compared to the distance between the X-ray source and the image beam receptor means.

Needle holder insertion means are shown at 73. This needle holder insertion means is shown as a means for inserting the needle holder normal to the compression plates. After inserting the needle holder the C-arm is tilted, for example by 20 degrees, and another exposure is made to determine whether or not the tip of the needle holder is sufficiently close to the center of the lesion. If it is sufficiently close, the hooked needle may be inserted through the needle holder and the needle holder may be withdrawn.

Figure 3B:
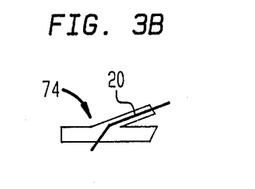
FIG. 3b shows an angled biopsy needle holder insertion device.

An alternative needle holder insertion means is shown in FIG. 3b at 74. This is an angled needle holder insertion means and is used when it is desired to insert the needle holder at an angle—preferably 20 degrees to the normal. In this procedure the C-arm angle is reversed, after partial insertion of the needle holder, to minus 20 degrees to the normal to check that the holder tip is sufficiently close to the lesion.

It should be understood that while an angle of 20 degrees is mentioned here, this invention encompasses any angles less than 90 degrees that provide the ability to assure that the needle point is sufficiently close to the desired lesion.

In FIG. 4 the breast compression means is shown as assembly 70 including upper and lower compression plates 69 and 71, respectively. The plate 69 is moveably mounted to vertical standard 67' for movement by handle 85 to compress the breast.

A horizontal plane movement means is shown and comprises a base plate 71 fixedly attached to pivot 66 or C-arm 61 for example.

Means such as handle and screw assembly 76 are provided for moving the compression mechanism in the horizontal plane in the Y direction i.e. transverse to the C-arm by moving Y-shift mount 77 in the Y direction relative to the base plate 75 with handle-screw arrangement 76. Similarly the compression assembly is moved in the horoizontal plane in the X direction i.e. toward and away from the C-arm by moving the X-shift mount 78 relative to the mount 77 with handle/screw combination 79. The horizontal adjustable movement mechanism expedites positioning the lesion along the axis of the X-ray beam. X and Y shift scales 80a and 80b are provided in a preferred embodiment.

Figure 5:
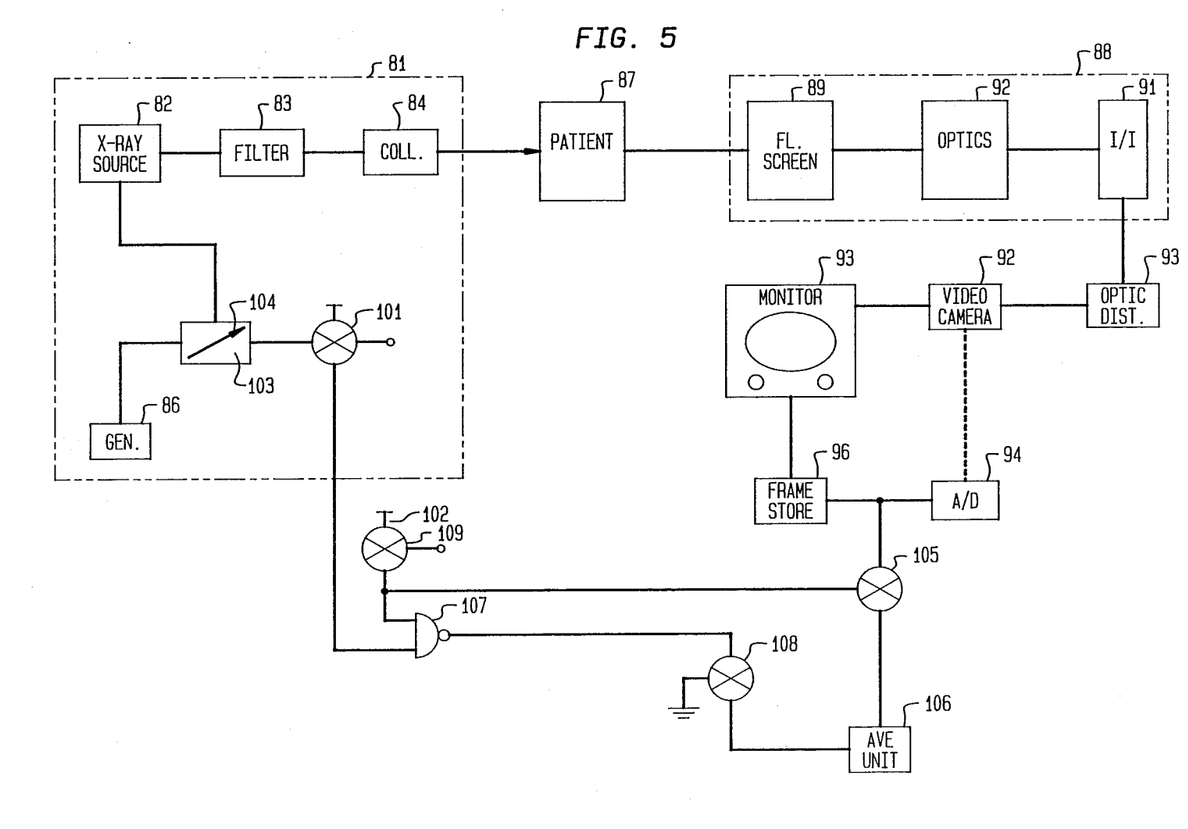
FIG. 5 is a block diagram of the inventive system showing the incremental dosage means.

Means are provided to maximize the image quality with the minimum X-ray dosage. More particularly as shown in FIG. 5 an X-ray beam source is provided at 81. The source comprises an X-ray tube 82, an X-ray filter 83 and an X-ray collimator 84. The X-ray tube is activated and energized by a generator 86. The patient is shown at 87. X-ray receptor means 88 are shown for receiving the X-rays after they pass through the patient. In the embodiment of the block diagram of FIG. 5 the receptor means comprises a fluorescent screen 89 optically coupled to an image intensifier means 91 by optics indicated at 92. The output of the image intensifier is coupled to a video camera 92. Coupling can be direct coupling or optical coupling which may include a distributor such as shown in FIG. 1. The optical coupler in FIG. 5 is shown at 93. A TV monitor displays the image taken by the TV camera after processing which includes analog-to-digital conversion as indicated at 94. A frame grabber or frame store 96 is extremely helpful, especially in situations where the radiologist increments the dosage.

Incremental dosage may be provided by operating two controls. For example, an exposure time control 101 selects the exposure time while the other control 102 increments the dosage. The operation of the exposure time control 101 connects the generator 86 to the X-ray tube 82 through a timing device 103. The timing device maintains the connection between the generator and the tube for the set time indicated by the arrow 104 and then disconnects the generator from the X-ray tube. When only the exposure time control 101 is operated, then the data acquired due to the dosage provided during the set time of 104 is averaged in the frame store to provide the TV monitor with an image. However, if both the exposure time control 101 and the dosage incremental control 102 are operated, then another electronic switch 105 is operated to cause the output of the analog-to-digital converter to be transmitted to an averaging unit 106. The averaging unit provides an average of a plurality of exposures, the averaged values are transmitted to the frame store to provide incrementally obtained average intensity data for the image.

When only the image exposure time control 101 is operated then a NAND gate 107 opens to operate a switch means 108 to "dump" the incrementally obtained average values by coupling the averaging unit contents to ground.

When both controls 101 and 102 are operated, then the gate 107 is prevented from operating. The electronic switch 109 maintains a signal on the other input of NAND gate 107. Thus, the radiologist is able to use a minimum dosage every time. If he uses a sub-minimal dosage and obtains an unclear image, he can then increment that dosage until he does obtain a clear image. Alternatively, the incremental dosage means may be incorporated in a micro-computer used for system control. It should be noted that the incremental dosage means finds usage in general X-ray systems and accordingly is not limited to mammographic biopsy needle holder locating systems.

Figure 6:
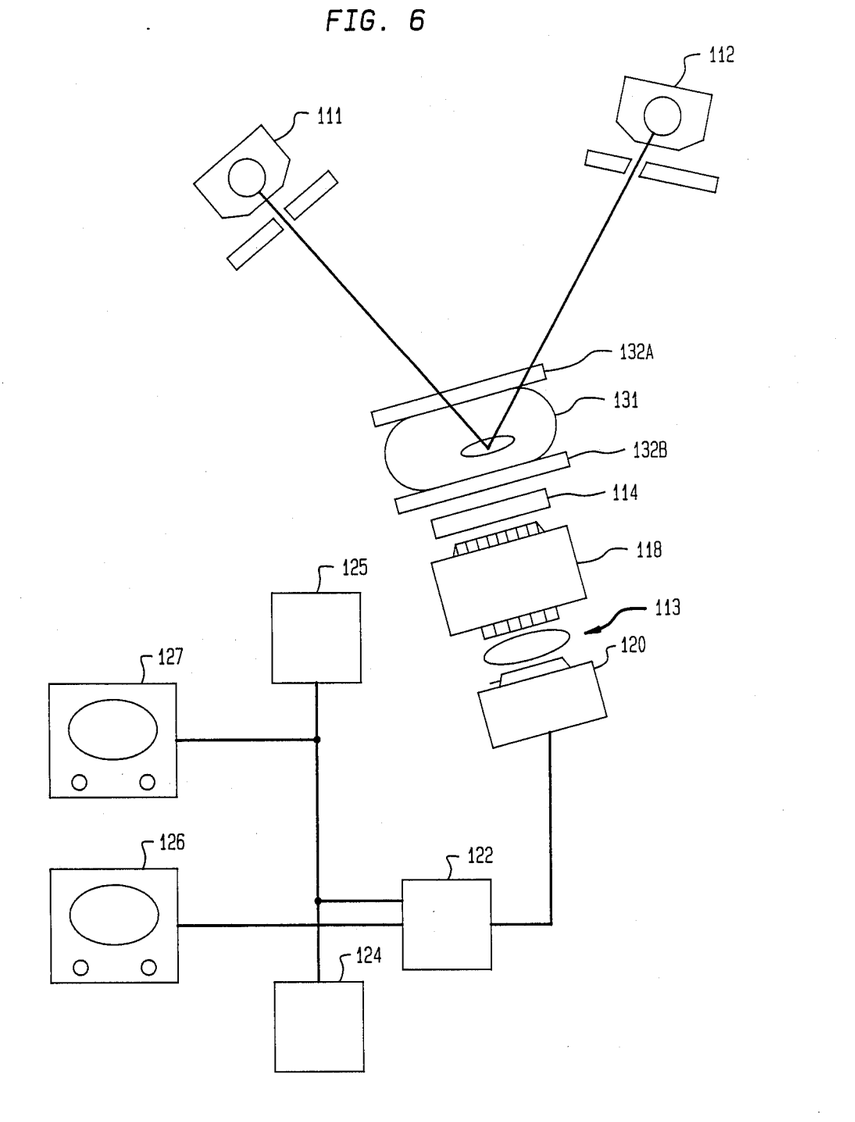
FIG. 6 is a diagram of a system using stereo in the embdiment of FIG. 1.

FIG. 6 indicates a system for obtaining a steroscopic image of the lesions within the breast. The steroscopic image is obtained by using dual X-ray sources. In the system of FIG. 6 a pair of X-ray tubes are shown at 111 and 112. The tubes are grid-controlled so that one can be turned off while the other is providing X-rays. Thus, only one tube provides X-rays at a time. Alternatively a switching arrangement can be provided to assure that only one tube is emitting X-rays at any given instant. An imaging chain 113 is shown. It includes fluorescent screen 116, image intensifier 118, video camera 120, image processor 122, frame grabbers 124, and display mean 126 and 127.

The X-rays pass through the patient's breast shown at 131 in a compression unit made of plates 132a and 132b. In a preferred embodiment a one inch X-ray film screen is optically coupled to a one inch high resolution image intensifier. The image intensifier output is coupled to a high resolution TV camera. The stereo image thus acquired enables the radiologist to immediately judge the depth of penetration of the biopsy needle holder from the two displays, while the breast is compressed.

Accordingly there is no need to release the breast with needles in it and recompress it in another direction. Similarly there is no need for repositioning the X-ray tube to determine the depth of needle holder penetration. Thus the improvement of FIG. 6 provides biopsy locating needle positioning which uses two X-ray sources along with the high intensity imaging equipment of FIGS. 1 and 2. The system can be applied using the folding mirror or prism described in conjunction with FIG. 2.

In operation the radiologist initially examines the preliminary X-ray films of the patient to determine the approximate region of the lesion in the breast. He then sets the patient in front of the breast compression means. The breast is compressed using the breast compression locating movement and locating means to approximately locate the region of interest of the breast along the axis of the X-ray beam so that the lesion is axial. An image is then acquired, either by film or fluoroscopically depending on whether a film or imaging chain X-ray receptor is being used. Corrections are then made to accurately locate the lesion in the axis of the X-ray beam. When this is done a needle holder is inserted. The needle holder insertion means of FIGS. 3a and 3b may be used. When using the needle holder itself the needle holder is adjusted so that its axis is normal to the compression plates. The needle holder is inserted when there is a minimum shadow cast by the needle holder. The needle holder is initially inserted into the breast for a short distance. Subsequently the C-arm is tilted so that the beam is now displaced by about 20 degrees and the image is checked to determine if the needle is sufficiently close to the lesion. Once the tip of the holder is sufficiently close to the lesion in the image, taken at a parallax angle, the needle is inserted through the holder until its tip lies within the lesion. At this time the needle holder is removed. Thus the needle holder and the needle can be inserted using the equipment provided herein without having to uncompress and recompress the breast. The time for locating the needle holder and inserting the needle is reduced from 20-30 minutes to approximately 5-8 minutes. When the imaging chain is used then it is important that a frame grabber is used to minimize the X-ray dosage. Thus one a sufficient increment of dosages is supplied to obtain a good image, then the image is held by the frame grabber and there is no necessity for continued dosage.

While the invention is described using specific embodiments it should be understood that these embodiments are described by way of example only and not as limitations on the scope of the invention.

What is claimed is:

1. A mammographic biopsy needle holder positioning system for locating a needle holder in a breast to identify a lesion therein that is to undergo biopsy, said system comprising:
   a biopsy needle holder adapted to be inserted into the breast,
   x-ray tube means for generating x-ray beams, said x-ray tube means being positioned to direct said x-ray beams so that they pass through the breast of the patient,
   breast compression means for compressing the breast to reduce the distance through the breast traversed by the x-ray beams, said breast compression means comprising first and second compression plates and means for moving said compression plates relative to each other to compress said breast therebetween,
   x-ray receptor means for receiving x-rays, said x-ray receptor means being located opposite the x-ray tube means for receiving the x-ray beams after they have traversed the breast and for obtaining a view thereof,
   C-arm means for holding said x-ray tube means and said x-ray receptor means aligned and spaced apart,
   a relatively immobile base means for supporting said breast compression means,
   means for mounting said breast compression means to said base means while enabling said breast compression means to move laterally and transversely on said base means relative to said C-arm means, and
   pivot means for mounting said C-arm means to said base means for supporting said C-arm means while enabling said C-arm means to pivot around said base means and said compression means for obtaining displays on said receptor means of different views of the biopsy needle holder inserted into the breast in accordance with the angular position of said C-arm means on said base means.

2. The system of claim 1 wherein said X-ray receptor means comprises film means for providing hard copy X-ray images.

3. The system of claim 1 wherein said X-ray receptor means comprises an imaging chain, said imaging chain comprising fluorescent screen means for providing fluoroscopic images of the breast traversed by said X-ray beams, said fluorescent screen means being coupled to an image intensifier means for intensifying said fluoroscopic images, video camera means coupled to the output of said image intensifier means for converting said intensified fluoroscopic images to video signals, image processing means for processing the video signals at output of said video camera means to provide images, and display means for displaying the images.

4. The system of claim 3 wherein said image intensifier means is optically coupled to said video camera means, said optical coupling including image splitting means to enable on line optically viewing the output of said image intensifier and further processing the output of said image intensifier.

5. The system of claim 1 wherein said different views comprise an initial view accomplished with the x-ray tube mounted to provide x-ray beams at an angle of about 20° to the normal to the compression plates, said needle holder being inserted coaxially with said base, and a second view at a parallax angle at approximately 20° from the first view.

6. A mammographic biopsy needle holder positioning system for positioning a needle holder to locate lesions in a patient's breast, said system comprising:
   a biopsy needle holder adapted to be inserted into the breast,
   x-ray source means for generating x-ray beams directed to pass through the breast of the patient,
   x-ray receptor means for receiving x-rays, said x-ray receptor means being located opposite the x-ray source for receiving the x-ray beams after they have traversed the breast and for obtaining a view thereof,
   compression means for compressing the breast substantially in the direction of the x-ray beams,
   tilting means for tilting the x-ray source and receptor means for obtaining images of the breast at different angles,
   said tilting means being constructed and arranged so as to tilt independently of said compression means but being attached to said compressing means, said compressing means including means for moving said compressing means, independently of said tilting means, in a plane traversed by x-ray beams from said x-ray source means,
   said x-ray receptor means comprising an imaging chain including fluorescent screen means for providing a fluoroscopic image, image intensifier, means coupled to said fluorescent screen means for intensifying the fluoroscopic image of the fluorescent screen,
   means for coupling a video camera to the output of said image intensifier means,
   means for processing the output of the video camera to obtain display data,
   means for providing a display from said display data, said processing means including storage means for storing the display data used to provide the display, means for incrementally energizing the x-ray source means, averaging means for averaging the averaging collected data obtained responsive to incrementally energizing the X-ray source means, means for transmitting said averaged data from said averaging means to said storage means as display data, and means for terminating the incremental energization when the displayed image is of a required quality to view the biopsy needle holder inserted into the breast.

* * * * *

UNITED STATES PATENT AND TRADEMARK OFFICE
CERTIFICATE OF CORRECTION

PATENT NO. : 4,821,727

DATED : April 18, 1989

INVENTOR(S) : Simha LEVENE et al.

It is certified that error appears in the above-identified patent and that said Letters Patent is hereby corrected as shown below:

At column 10, line 46 of the printed patent, "compression" should be changed to ---compressing---.

At column 10, line 52 of the printed patent, "compression" should be changed to ---compressing---.

At column 10, line 60 of the printed patent, the second occurence of "," should be deleted.

At column 11, lines 5-6 of the printed patent, "averaging collected" should be deleted.

Signed and Sealed this

Sixth Day of February, 1990

*Attest:*

JEFFREY M. SAMUELS

*Attesting Officer*    *Acting Commissioner of Patents and Trademarks*